Figure 1:
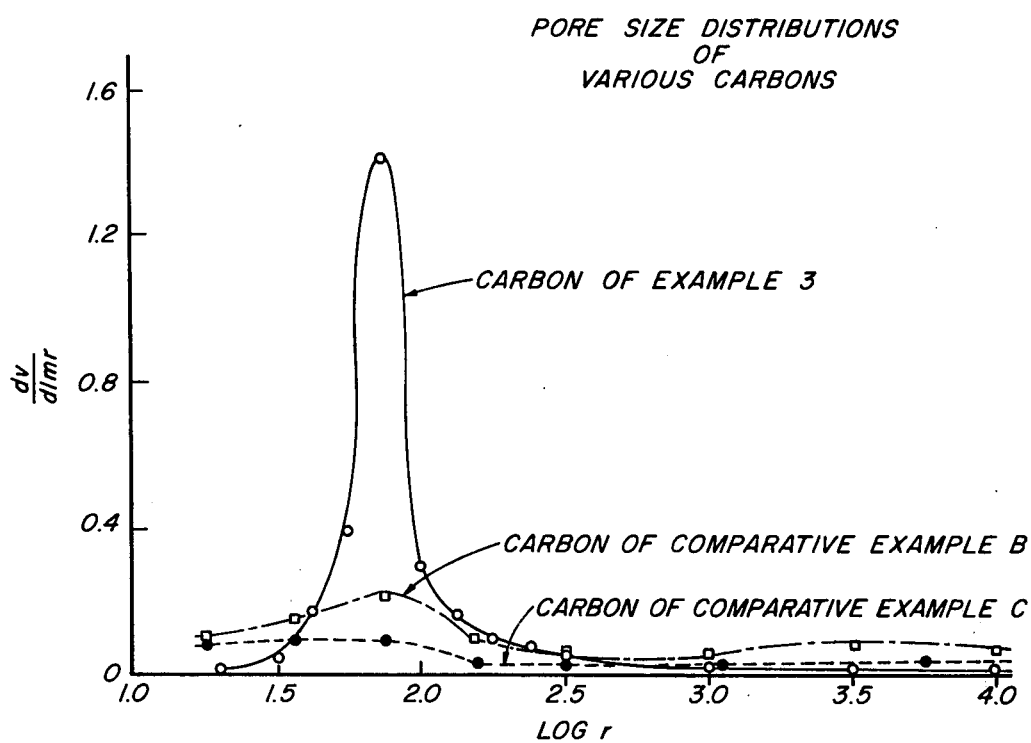

United States Patent [19]

Schmitt, Jr. et al.

[11] 4,031,137

[45] June 21, 1977

[54] CATALYSTS BASED ON CARBON SUPPORTS AND USE IN CATALYTIC DEOXIDATION PROCESS

[75] Inventors: Joseph Lawrence Schmitt, Jr., Bethel, Conn.; Philip Leroy Walker, Jr., State College, Pa.; George Augustus Castellion, Stamford, Conn.

[73] Assignee: American Cyanamid Company, Stamford, Conn.

[22] Filed: Feb. 11, 1976

[21] Appl. No.: 657,115

Related U.S. Application Data

[62] Division of Ser. No. 559,997, March 19, 1975, Pat. No. 3,978,000.

[52] U.S. Cl. .................... 260/559 AT; 252/447; 252/477 R; 260/580
[51] Int. Cl.² .................................. C07C 103/19
[58] Field of Search ............... 260/559 AT, 580

[56] References Cited

UNITED STATES PATENTS

| | | | |
|---|---|---|---|
| 3,019,260 | 1/1962 | McCormick | 260/559 AT |
| 3,073,865 | 1/1963 | Spiegler | 252/447 |
| 3,127,356 | 3/1964 | Hamilton et al. | 252/447 |
| 3,146,243 | 8/1964 | Andersen et al. | 252/447 |
| 3,154,584 | 10/1964 | Gardner et al. | 260/580 |
| 3,403,179 | 9/1968 | Zambrano | 260/559 AT |
| 3,483,251 | 12/1969 | Zambrano | 260/559 AT |
| 3,499,034 | 3/1970 | Gonzalez | 260/580 |
| 3,579,579 | 5/1971 | Hlavka et al. | 260/559 AT |
| 3,736,265 | 5/1973 | Suggitt | 252/447 |

*Primary Examiner*—Arthur P. Demers
*Attorney, Agent, or Firm*—William J. van Loo

[57] ABSTRACT

Carbon particulates comprising carbon black spheres and a carbon binder having large pores as well as desirable pore size distribution are disclosed which serve as catalyst supports. The support carrying an effective amount of an activator is an active catalyst composition for a variety of reactions including reduction reactions.

13 Claims, 2 Drawing Figures

CATALYSTS BASED ON CARBON SUPPORTS AND USE IN CATALYTIC DEOXIDATION PROCESS

This is a division, of application Ser. No. 559,997, filed Mar. 19, 1975, now U.S. Pat. No. 3,978,000, issued Aug. 31, 1976.

This invention relates to a catalyst composition comprising a porous carbon particulate made up of carbon black spheres and a carbon binder and, carried thereon, at least one activator. More particularly this invention relates to porous carbon catalysts of controlled pore size distribution and to improved catalytic processes employing same.

This application is directed to porous carbon catalysts and to processes employing same. Copending application Ser. No. 559,933 filed on even date herewith now abandoned, is directed to the porous carbon particulates, to the method of preparation thereof, and to the use thereof as selective adsorbents.

Carbons containing macropores can be useful as catalyst supports, particularly where large reactant molecules, such as those in the pharmaceutical and petroleum industries are involved. For example, such a carbon particle activated with a noble metal such as platinum or rhodium, could be used for catalyzing hydrogenation reactions of molecules containing several benzene rings.

Porous carbons have been obtained in the prior art by activation of a suitable material such as coal or wood charcoal, with oxidizing agents. These oxidizing agents, e.g. $O_2$, $CO_2$, steam, and the like, react away portions of the carbon, leaving behind pores. Carbons with controlled pore size distribution cannot be made by this procedure since new pores are continuously forming while existing pores are constantly being enlarged. This results in a broad distribution of pore sizes including many small pores, i.e., well below 20 angstrom units, as activation is continued. Thus, it has been difficult to obtain porous carbons containing predominantly transitional pores (diameter 20–200 angstrom units) as well as carbons having a narrow range of specific pore sizes.

In addition to the problem of controlling pore size distribution in prior art carbons, the reacting away of carbon to provide pores creates additional problems. When large pores are desired in the carbon, the reacting away of the carbon weakens the mechanical strength of the final structure. The reacting away of carbon increases the percent of ash in the residual carbon and ash contents of 5–10 weight percent are normal. In addition, carbons prepared by the prior art procedure contain many surface groups containing oxygen which may not be desired, when specific catalytic materials are considered.

The preparation of carbon structure by other procedures is also known in the prior art. In many instances, however, such structures contain significant amounts of material other than carbon. In other instances, the particular carbon structure is prepared for uses other than as catalyst supports so that no specific requirements as to porosity or pore size distribution are necessary.

Thus, there continues to exist the need for substantially pure carbon structures that have desirable levels of porosity or controlled pore size distribution and are free of or improved with respect to deficiences of the prior art carbons, which structures serve admirably as supports for catalyst materials. Such a development would fill a long-felt need in the art and provide a notable advance in the art.

Accordingly, it is a primary object of the present invention to provide a catalyst composition comprising an activator carried on a porous carbon structure having pores of controlled size distribution.

In accordance with the present invention, there is provided a catalyst composition comprising a porous carbon particulate support comprising carbon black spheres in packed relationship and a carbon binder, said spheres having a particle size in the range of about 80 to 5000 angstrom units and said particulate having pore size distribution exhibiting peaks at a pore radius in excess of 10 angstrom units and, carried on said support, an effective amount of an activator. Preferably, the particulate support will have a composition of at least 99 weight percent carbon. In preferred embodiments, the support will have a pore volume of at least 0.2 cubic centimeters per gram, more preferably 0.4 to 1.0 cubic centimeters per gram, showing peaks at a radius of at least 10 angstrom units, preferably in the range of 10–250 angstrom units. In another preferred embodiment, the support has a pore size distribution exhibiting maximum pore radius in the range of 40–100 angstrom units. In still another preferred embodiment, the support will contain less than 1 weight percent of ash. In yet another preferred embodiment, the carbon black spheres used to prepare the support have an average diameter in the range of 80–300 angstrom units.

In accordance with the present invention pores of the carbon particulate are formed by packing together of suitable carbon black spheres and binding the spheres together in packed relationship with a carbon binder. The use of the carbon binder allows the carbon particulate to possess improved mechanical strength. When the carbon black spheres packed and bonded together are of substantially the same size and relatively small, a narrow range of pore size distribution will arise and the particulate will possess good mechanical strength. The particular range of pore sizes and distribution thereof will vary with particle size of the carbon black spheres selected with the variations which occur within a designated size. Thus, if larger carbon black spheres are used, the interstitial space or pores will be larger, while the use of spheres of varying diameter will result in a wide range of pore sizes.

In the prior art carbon structures, when large pores are desired, extensive oxidation is carried out to provide the pores and the loss of carbon thus occasioned greatly weakens the resulting structure. Contrary to this, the carbon binder of the present invention provides good mechanical strength in conjunction with large pore sizes.

The carbon particulates of the present invention will, in preferred embodiments, have a large surface area resulting from pores in the transitional range, i.e., 20 to 200 angstrom units, and from macropores, i.e., pores greater than about 200 angstrom units. The number of pores in the transitional and macropore range will be much greater than can be achieved by prior art procedures.

Since the carbon black spheres used in the fabrication of carbon particulates of the present invention are of a high state of purity, the resulting particulates will be much purer than prior art carbon structures obtained by the conventional oxidation procedures. Normally, the prior art structures contain from 5-10 weight percent of ash. Carbon particulates of the present invention, to the contrary, contain less than about 1 weight percent of ash. In addition, since the carbon particulates of the present invention are prepared without the use of oxidizing agents to react away carbon, the carbon particulates of the present invention will contain considerably less surface oxygen-containing groups than the conventional carbon structures.

Carbon particulates of the present invention are useful as catalyst supports wherein the increased porosity and desirable pore size distribution provide advantages over prior art carbon structures, particularly when large reactant molecules are involved. Large reactant and product molecules will have less difficulty penetrating the pore volume of the carbon particulates of the present invention because of the presence of ample porosity of increased pore diameter. Thus, the catalyst will provide a higher effective activity due to the improved mass transport properties present in the carbon particulate of the present invention. In addition, since active catalyst material deposited in pores inaccessible to large reactant molecules is wasted, the present invention provides catalyst supports in which the amount of wasted catalytically active material is minimized.

Carbon blacks are formed by the thermal decomposition of gaseous and liquid hydrocarbons. Two main manufacturing processes are employed. In the channel process, carbon black is collected by impingement of small, natural gas diffusion flames on cool channel iron surfaces. By altering the size of the burner tip and its distance from the channel surface, the particle size of the carbon black can be varied.

The furnace combustion process, which currently produces the greater amount of carbon black, uses larger diffusion flames to combust natural gas and/or liquid hydrocarbon in firebrick-lined furnaces. Carbon blacks with considerably larger particle size than channel carbon black can be produced.

Carbon particles useful in the present invention may be of any shape that can be packed and bonded together to provide particulates which have the desired porosity. Particularly suitable are available carbon blacks made by the above processes, which generally have an average diameter from about 80 to 5000 angstrom units and a porosity that varies with the specific preparative method employed. These carbon blacks are revealed by electron photomicrographs to consist of ultimate particles which appear to be essentially spherical. For convenience, therefore, in the present application and claims, the carbon black particles are referred to as spheres but is to be understood that the present invention is inclusive of other shapes, such as oval-shaped, round-cornered squares, rectangles, triangles, and the like as long as such particles upon packing and bonding give rise to the porosity desired.

Carbon black spheres useful in the present invention may be selected from any that are commercially available. Selection is based on the porosity and pore size distribution desired in the carbon particulate to be selected in accordance with the present invention. When small pores of a narrow pore size distribution are desired, carbon black spheres of small particle size and narrow variation in particle size are selected. When large pores are desired, carbon black spheres of large particle size are selected. When a wide range of pore sizes are desired, mixtures of carbon black spheres of varying particle sizes are selected.

In addition to the carbon black spheres, it is also necessary to employ a binder for the spheres that are to become arranged in packed relationship. The binder is a substance which when heat-treated in an inert or non-oxidizing atmosphere yields a high proportion of carbon. Generally a carbon yield greater than about 20 weight yield is desirable when heat-treatment is carried out at 600° C. in an atmosphere of nitrogen. Carbon yield is the weight of the carbon residue divided by the weight of starting material and multiplied by 100. Materials which meet this qualification include polymers such as poly(furfuryl alcohol), polyacrylonitrile; resins such as phenol-formaldehyde, phenol-benzaldehyde; and certain natural materials such as coal tar pitch. Preferably the binder will be a thermosetting resin. Enough binder is required to hold the carbon structure together after carbonization of the binder. Normal ratios of carbon black spheres to binder will be from about 10:1 to 0.1:1, preferably 5:1 to 1:1, on a weight basis based on the amounts of material employed prior to heat-treatment to carbonize the binder.

It is also necessary to employ a mixing medium to provide intimate mixing of the binder and the carbon black spheres. Preferably the mixing medium will be a solvent for the binder but it is possible to employ the binder in emulsified or dispersed form in the mixing medium. The mixing medium should be volatile enough so that gentle heating (100°–150° C.) will effect volatilization and eliminate the possibilities that the mixing medium will interfere with or take part in carbonization of the binder. Suitable mixing media include acetone, methyl isobutyl ketone and other ketones, benzene, pyridine, water and the like. The amount of mixing medium should be enough to ensure intimate mixing and may vary widely. Generally the amount of mixing medium will be such as to provide the binder as about a 5 to 50 weight percent solution or emulsion, preferably about 10 to 20 weight percent solution.

Once the carbon black spheres, the binder, and the mixing medium are selected and intimately admixed, the resulting composition is processed so as to pack the carbon black particles into a suitable structure. Such processing may involve extrusion, pelletizing, pilling, tabletizing and such other forms of molding are conventionally employed in forming structured particles. It is also possible to employ rolling mills and flakers to provide a formed structure of packed carbon although such procedures do not usually form uniform particles as in the case of molding. It is generally preferred to employ extrusion to obtain the carbon structure. The carbon structure thus obtained is referred to as a "green body". The green body is subjected to gentle heating to volatize the mixing medium and then subjected to carbonization at elevated temperature in an inert or non-oxidizing atmosphere so as to convert the binder to carbon. The resulting carbon structure may be utilized in the form obtained or it may be subdivided by crushing or grinding, if desired. It can also be further modified by treatment with an oxidizing agent, if desired, although it is generally preferable to take advantage of the desirable properties achieved in the absence of oxidation of the carbon structure.

As has been indicated, the carbon structures of the present invention can be prepared in a wide variety of pore volume and pore size distribution. In particular embodiments, the carbon structures will have a larger surface area in the large pore region than previously available carbons, the large-pores occurring in a narrow size range, if desired. When used as a catalyst support, a carbon structure of such type will provide higher effective activity due to improved mass transport properties it possesses. This type of carbon, by virtue of its method of preparation, will also have a much lower ash content (impurity level) than conventional oxidized carbons.

The catalyst composition of the present invention comprises the carbon support described and, carried thereon, an effective amount of an activator. The activator and amount thereof employed with depend upon the particular reaction to be catalyzed and the relative effectiveness of the activator in the reaction. There are numerous reactions that are effectively catalyzed by supported activators and many wherein carbon is a useful support. In general, any catalyst composition based on a carbon support which is known to be useful in the prior art will be advantageously prepared using the carbon support of the present invention because of the greater proportion of pores of larger radii of the present supports and the attendant reduction in wasted catalyst material, especially where large reactant molecules are involved. Thus, no new teachings as to activators or amounts thereof are necessary since the present invention contemplates conventional activators on an improved carbon support in the conventional reactions.

The catalyst compositions of the present invention exhibit improved activity in conjunction with hydrogenation reactions and are illustrated in this type of reaction. Particularly effective activators in this type of reaction are the platinum metals, which include ruthenium, rhodium, palladium, osmium, iridium, and platinum. Effective amounts may range from about a thousandth to about 10 weight percent or more, depending upon the reaction involved and the metal employed. In such reactions, activator usage and amounts will conform to conventional teachings with improved activity being obtained by use of the support of the present invention. Preferred reactions are in the reduction of 6-hydroxy hydronaphthacenes, as described in U.S. Pat. No. 3,019,260, issued Jan. 30, 1962 to McCormick et al. and related compounds. Another preferred reaction is in the reduction of 2,4-dinitrotoluene and related compounds to the corresponding diamines.

Additional reactions which can be advantageously carried out using catalyst materials of the present invention are those involving reductive alkylation of 7-(N,N'-dicarbobenzyloxyhydrazino)tetracycline and 7-(N,N'-dicarbobenzyloxyhydrazino)-11a-halotetracyclines. Typical starting materials which are effectively reductively alkylated include:

7-(N,N'-dicarbobenzyloxyhydrazino)tetracycline,
7-(N,N'-dicarbobenzyloxyhydrazino)-5-hydroxytetracycline,
7-(N,N'-dicarbobenzyloxyhydrazino)-6-demethyltetracycline,
7-(N,N'-dicarbobenzyloxyhydrazino)-11a-chloro-6-demethyltetracycline,
7-(N,N'-dicarbobenzyloxyhydrazino)-6α-methyl-6-deoxytetracycline,
7-(N,N'-dicarbobenzyloxyhydrazino)-11a-bromo-6β-methyl-6-deoxytetracycline,
7-(N,N'-dicarbobenzyloxyhydrazino)-6-demethyl-6-deoxytetracycline,
7-(N,N'-dicarbobenzyloxyhydrazino)-11a-chloro-6-demethyl-6-deoxytetracycline,
7-(N,N'-dicarbobenzyloxyhydrazino)-11a-bromo-6-demethyl-6-deoxytetracycline,
7-(N,N'-dicarbobenzyloxyhydrazino)-11a-fluoro-6-demethyl-6-deoxytetracycline,
7-(N,N'-dicarbobenzyloxyhydrazino)-6-demethyl-6-deoxy-6-methylene-5-hydroxytetracycline,
7-(N,N'-dicarbobenzyloxyhydrazino)-6-deoxy-5-hydroxytetracycline, and the like in the form of the free bases or acid salts. Typical products obtained by such reductive alkylation include:

7-dimethylamino-demethyl-6-deoxytetracycline,
7-diethylamino-6-demethyl-6-deoxytetracycline,
7-isopropylamino-6-demethyl-6-deoxytetracycline,
7-isopropylaminotetracycline,
7-isobutylamino-5-hydroxytetracycline,
7-dimethylamino-6-demethyltetracycline,
7-di-(n-propyl)amino-6-deoxy-6α-methyltetracycline,
7-di(n-butyl)amino-6-deoxy-6β-methyltetracycline,
7-methylamino-6-demethyl-6-deoxy-6-methylene-5-hydroxytetracycline and
7-ethylamino-6-deoxy-5-hydroxytetracycline.

Such tetracyclines are biologically active and possess the broad-spectrum anti-bacterial activity of the previously known tetracyclines. In particular, the 7-dimethylamino-6-demethyl-6-deoxytetracycline, 7-diethylamino-6-demethyl-6-deoxytetracycline and 7-isopropylamino-6-demethyl-6-deoxytetracycline possess extraordinary activity both orally and parenterally against Staphylococcus aureus, strain Smith, and Staphylococcus aureus, strain Rose, infections in mice.

It is also known that catalysts based on carbon supports are useful in hydrodesulfurization of petroleum residua. In such reactions, a combination of an activator and promoter are generally employed. The activator is generally selected from molybdenum and tungsten and the promoter from cobalt and nickel with the metals being in the form of their sulfides in use.

Figure 2:
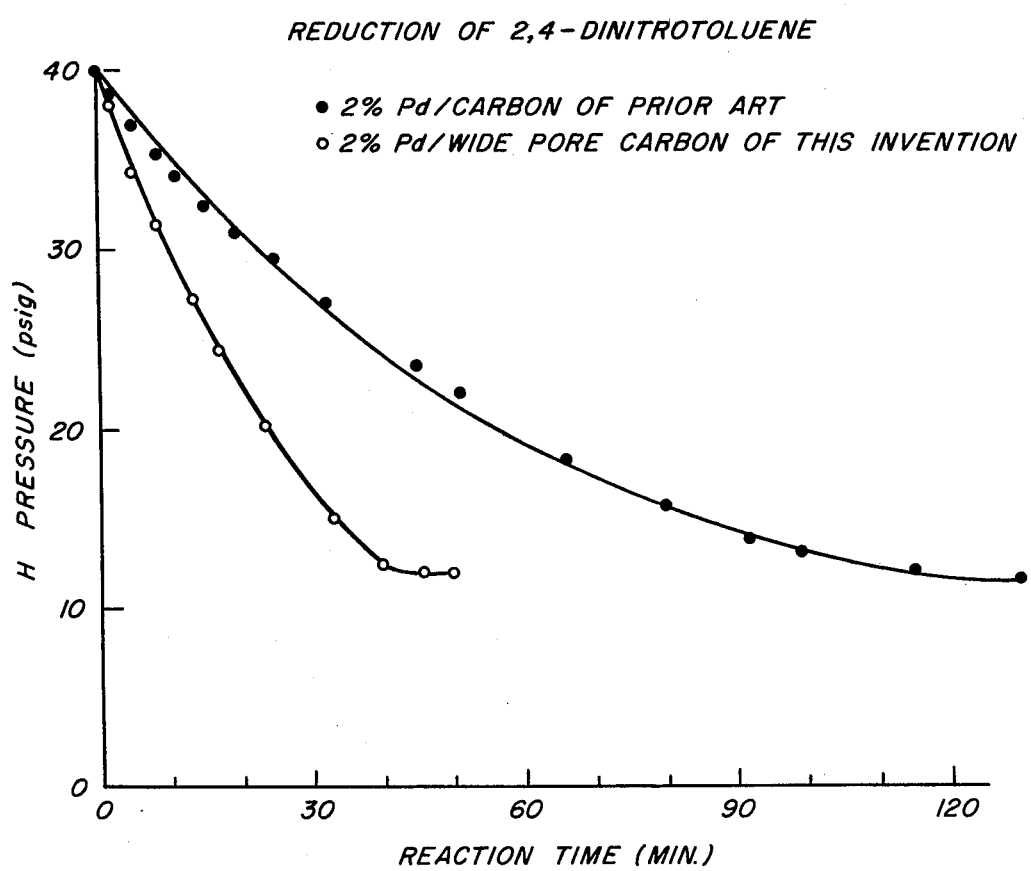

The invention may be further understood by references to FIG. 1 which shows comparative pore size distribution of various carbons and FIG. 2 which shows comparative effectiveness of catalysts prepared using as substrates carbon particulates of the present invention and typical prior art carbon particulate.

The invention is more fully illustrated by the examples which follow wherein all parts and percentages are by weight unless otherwise specified.

In the examples which follow, reference is made to certain physical properties of the particulate supports obtained. These properties are obtained in accordance with conventional methods employed in the art of catalyst supports.

Pore volume may be obtained by mercury penetration or water adsorption. The latter is a preferred method because it is easily performed and has an accuracy of ± 10%. In the water adsorption procedure, a small quantity of support (1-2 grams) is weighed into a glass dish. Water is slowly poured onto the support until no more is adsorbed. Excess droplets are carefully removed by blotting and a reweighing is made. Assuming that one gram of water occupies one cubic centimeter, the pore volume is calculated from the initial and final weights of the support.

Surface area is measured by a low temperature nitrogen adsorption technique which is reported in J. Am. Chem. Soc., 60, 309 (1938), with modifications as reported in Anal. Chem., 30, (1958) and Anal. Chem., 34, 1150 (1962).

COMPARATIVE EXAMPLE A

Into 12 milliliters of water were added 10 grams of carbon black spheres having an average particle diameter of 120 angstrom units and a surface area of 850 square meters per gram. After hand mixing, the resulting composition was extruded through a hole of 1/16 inch diameter using a piston-type extruder operating at a pressure of 2000 pounds per square inch gauge. The resulting extrudates were dried in air at 110° C. and then heated in flowing nitrogen at 600° C. for 1 hour. The product was obtained in the form of cylindrical pellets. Properties are given in Table I.

EXAMPLE 1

A furfuryl alcohol polymer was prepared by mixing 200 milliliters of furfuryl alcohol, 200 milliliters of water, and 1 milliliter of concentrated $H_2SO_4$. The mixture was heated at 90° C. for 10 minutes. The dark polymer obtained was washed twice with water and then stored in a closed bottle.

In 100 ml. of acetone was dissolved 10 grams of the furfuryl alcohol polymer thus prepared. The resulting solution was added to 40 grams of carbon black spheres having an average particle diameter of 850 square meters per gram. The resulting composition was thoroughly mixed using a Sunbeam Mixmaster. The mixture was then extruded through a hole of 1/16 inch diameter using a piston-type extruder operating at 800–2000 pounds per square inch gauge.

The resulting extrudates were heated overnight at 110° C. to volatilize all of the acetone present and then carbonized in a tube furnace under flowing $N_2$. A temperature of 600° C. was reached in about 1 hour and held for 1 hour. The extrudates were then cooled to room temperature under flowing nitrogen. The product was obtained in the form of cylindrical pellets. Properties are also given in Table I.

EXAMPLE 2

The procedure of Example 1 was repeated in every essential detail except that 20 grams of a commercial phenolformaldehyde resin was substituted for the furfuryl alcohol polymer of Example 1 and the extrusion pressure was 2400 psig. Properties of the resulting pellets are also given in Table I.

TABLE I

PROPERTIES OF CARBON PARTICULATES

| EXAMPLE | BINDER | BINDER AMOUNT[1] | PORE VOLUME[2] | CRUSH STRENGTH[3] |
|---|---|---|---|---|
| Comparative A | None | 0 | 1.00 | 1.2 |
| 1 | Poly(furfuryl alcohol) | 25 | 0.99 | 5.4 |
| 2 | Phenol-formaldehyde resin | 50 | 0.62 | 7.7 |

[1]Weight % based on weight of carbon black
[2]Cubic Centimeters per gram
[3]Pounds Table I illustrates the importance of the binder in obtaining improved particulate strength. In can be seen that use of 25% binder resulted in a 4.5 fold increase in strength with essentially no loss in pore volume. Use of higher amounts of binder results in further increases in strength but results in lower pore volumes. Thus, if lower pore volumes can be tolerated, higher binder usage may be desirable.

EXAMPLE 3

In 75 ml. of acetone were dissolved 7.5 grams of poly(furfuryl alcohol) prepared as in Example 1. To this solution were added 30 grams of the carbon black spheres as used in Example 1. After thorough mixing, the resulting composition was extruded as in Example 1 using 250–500 psig extrusion pressure. The extrudates were dried overnight and then carbonized as in Example 1. Properties of the resulting pellets are given in Table II and FIG. 1.

COMPARATIVE EXAMPLE B

For comparison purposes, a commercially available carbon prepared by oxidation of carbon was selected. This carbon is sold under the tradename Darco Granular and was in the form of grains 12 × 20 mesh. Properties are also given in Table II and FIG. 1.

COMPARATIVE EXAMPLE C

For comparative purposes, another commercially available carbon prepared by oxidation of carbon was selected. This carbon is sold under the tradename Columbia Type L and was in the form of grains of 12 × 20 mesh. Properties are also shown in Table II and FIG. 1.

PROPERTIES OF CARBON PARTICULATES

| EXAMPLE | PORE VOLUME[1] | SURFACE AREA[2] | CRUSH STRENGTH[3] |
|---|---|---|---|
| 3 | 0.92 | 530 | 3.1 |
| Comparative B | 1.07 | 580 | 2.3 |
| Comparative C | 0.86 | 1235 | 5.7 |

[1]cc/gram
[2]m²/gram
[3]lbs.

In FIG. 1 are shown the pore size distribution for the carbons of Example 3, Comparative Example B, and Comparative Example C as obtained by mercury porosity [see Orr, C., Powder Technol. 3, 117 (1969–70)]. In the figure, the change in pore volume with respect to the change in the natural logarithm of the pore radius is plotted against the logarithm to the base 10 of the pore radius. As can be seen by the figure, the pore size distribution curves illustrate the major difference of carbon particulates of the present invention, which have many more pores in the region of radii of 40–100 angstrom units while many of the pores of the comparative carbons are too small to be measured by mercury penetration.

EXAMPLES 4–7

In these examples, a series of carbon particulates were prepared following the procedure of Example 3 in every essential detail except that carbon black spheres of different particle size were employed in separate preparations. Properties of the carbon black spheres employed and of the resulting carbon particulates are given in Table III.

TABLE III

| | CARBON BLACK SPHERES | | | EXTRUDATE PROPERTIES | | |
|---|---|---|---|---|---|---|
| EX. | AVERAGE DIAMETER[1] | SURFACE AREA[2] | SPHERES/ BINDER RATIO[3] | SURFACE AREA | PORE VOLUME[4] | RADII PEAKS AT[1] |
| 4 | 120 | 850 | 4 | 550 | 0.95 | 12,65 |
| 5 | 300 | 230 | 3 | 150 | 0.43 | 18 + broad dist to > 200 |
| 6 | 160 | 380 | 3 | 275 | 0.80 | 95 |
| 7 | 150 | 550 | 4 | 400 | 0.95 | 18,95 |

Notes:
[1]Angstrom Units
[2]Meters$^2$/gram
[3]Based on weight before carbonization
[4]cc/gram It can be seen from Table III that the physical properties of the catalyst particulates of the present invention may be varied by varying the size of the carbon black spheres or the ratio of spheres to binder. It is evident that the pore size of the carbon particulates can be shifted toward larger sizes by using carbon black spheres of larger average particle size.

EXAMPLE 8

In this example a catalyst was prepared by depositing rhodium metal on catalyst particulates prepared in accordance with Example 3.

In 20 ml. of water were dissolved 3.74 grams of RhCl$_3$.3H$_2$O and the resulting solution was added to 180 ml of dimethylformamide in a 500 ml bottle. To the mixture was added 10.5 grams of catalyst particulate of Example 3 and the mixture was hydrogenated at 50 psig. using a Parr shaker to deposit rhodium metal on the carbon particulates. When H$_2$ uptake was complete, the catalyst was filtered and washed with water, and stored in an approximately 50% water-wet state.

COMPARATIVE EXAMPLE D

In this example a catalyst was prepared by depositing rhodium metal on commercially available carbon particulates prepared by conventional oxidation procedures to provide porosity.

The procedure of Example 8 was followed in all essential details except that the carbon particulates were those commercially available under the tradename Norit SGX.

EXAMPLE 9

In this example, the catalysts prepared in Example 8 and Comparative Example D were evaluated in the process of catalytic reduction of 6-hydroxy hydronaphthacenes, as described in U.S. Pat. No. 3,019,260, issued Jan. 30, 1962 to McCormick et al. For testing, catalysts were prepared as in Example 8 except that the amount of RhCl$_2$.3H$_2$O was varied so that catalysts were obtained which contained either 6% metal or 12% metal based on the total weight of the catalyst composition. The catalyst was added in the amount of 0.003 or 0.006 troy ounces of rhodium metal depending on whether the catalyst contained 6 or 12% metal, respectively to 40 ml. of methyl cellosolve and reduced at 35° C. for 1 hour and 40 psig hydrogen pressure using a Parr shaker. A solution containing 6-demethyltetracycline dissolved in methyl cellosolve was then added to provide a concentration of 60 grams per liter of 6-demethyltetracycline. The solution was then hydrogenated at 35° C. for 1 hour and 40 psig. hydrogen pressure. After 1 hour of reduction, samples were taken for analysis and concentrations of reactant and product, 6-demethyl-6-deoxytetracycline. Results are given in Table IV.

TABLE IV

| CATALYTIC REDUCTION OF 6-DEMETHYLTETRACYCLINE | | | |
|---|---|---|---|
| Catalyst of Example | Rhodium (%)[1] | Conversion % After 1 Hour | Selectivity To 6-Demethyl 6-Deoxytetracycline |
| Comparative D | 6 | 45 | 0.80 |
| 8 | 6 | 57 | 0.88 |
| Comparative D | 12 | 55 | 0.81 |
| 8 | 12 | 66 | 0.84 |

[1]Percent based on total of catalysts composition

The data of Table IV show that catalysts prepared using as carriers the carbon particulates of the present invention provide both a greater activity and greater selectivity than similar catalysts prepared using conventional carbon supports. Note that the catalyst of the invention is more active at 6% metal than the comparative catalysts at 12% metal. It is believed that the superior results achieved by catalysts prepared by use of carbon particulates of the present invention is due primarily to the increased number of pores in the 50–200 angstrom units range of pore radii since these pores would be large enough to allow unrestricted entry of the large reactant molecules.

EXAMPLE 10

Using the carbon particulate prepared in accordance with Example 3, a catalyst was prepared.

To 100 ml. of water was added 0.17 gram of PdCl$_2$ (60% Pd) and then 4.0 ml. of 10% aqueous HCl was added. The composition was stirred for about 40 minutes to dissove the PdCl$_2$. To the solution was then added 4.9 grams of the carbon particulates of Example 3 in a particle size of 40 × 60 mesh and an additional 15 minutes of stirring was effected. The pH of the mixture was raised to 9.5–10.5 by the addition of 2M NaOH. The pH was maintained for 15 minutes by drop wise addition of NaOH as necessary. A total of 2.5–3.0 ml. of caustic was required. The catalyst was then separated by filtration and washed with 300 ml. of water. The water-white filtrate indicated that all of the palladium was taken up by the carbon. The catalyst was bottled and stored in a state of 50% water wet. Before use, an aliquot was dried 30 minutes at 125° C. to determine its actual wetness.

COMPARATIVE EXAMPLE E

The procedure of Example 10 was followed in every material detail except that in place of the carbon particulate prepared in accordance with Example 3, there was substituted the carbon particulate of Comparative Example C in a particle size of 40 × 60 mesh.

EXAMPLE 11

In this example, the catalysts prepared in Example 10 and Comparative Example E were evaluated in the process of catalytic reduction of 2,4-dinitrotoluene.

In a mixture of 10 ml. of water and 60 ml. of isopropanol in a 500 ml. Parr bottle was dissoved 0.91 gram (0.005 mole) of 2,4-dinitrotoluene. Enough catalyst in the 50% water-wet state was added to provide 0.20 gram of catalyst on a dry basis, the catalyst corresponding to 2% Pd on carbon. The bottle was attached to the Parr hydrogenator and flushed 3 times with hydrogen. It was then pressurized with hydrogen to 40 psig. and isolated. Shaking of the bottle was carried out and the extent of reaction was followed by noting the hydrogen-pressure drop on the gauge. The reaction bottle was maintained at 35 ± 0.5° C. using a thermostated water jacket. Results of the reaction are shown in FIG. 2.

From FIG. 2 it can be seen that the reaction is complete in approximately 45 minutes when the catalyst prepared in accordance with Example 10 is employed. On the other hand, when the catalyst prepared in accordance with Comparative Example E is employed a reaction time of approximately 115 minutes is required. Again, it appears that the superior results obtained with the catalysts of the invention is due primarily to the wide pores it contains and to the smaller mass transfer limitations imposed thereby.

We claim:

1. A process for the catalytic reduction of 6-hydroxynaphthacenes so as to form the corresponding 6-deoxy derivative thereof which comprises reducing a polar solvent solution of a 6-hydroxy hydronaphthacene with hydrogen in the presence of a catalyst composition comprising a porous carbon particulate support comprising carbon black spheres in packed relationship and bonded with a carbonized binder, said spheres having a particle size in the range of about 80 to 5000 angstrom units and said particulate having a pore volume of at least about 0.2 cubic centimeter per gram and a pore size distribution exhibiting peaks at a pore radius in excess of 10 angstrom units and, carried on said support, an effective amount of a platinum group metal, until about one mole of hydrogen has been absorbed for each mole of starting material used, and recovering the 6-deoxy derivative so formed.

2. The process of claim 1 wherein said support has a pore volume of at least about 0.2 cubic centimeter per gram.

3. The process of claim 1 wherein said support has a pore volume of about 0.4 to 1.0 cubic centimeter per gram.

4. The process of claim 1 wherein said support has a composition of less than about 1 weight percent of ash.

5. The process of claim 1 wherein said carbon black spheres have a particle size in the range of about 80–300 angstrom units.

6. The process of claim 1 wherein said support has a pore size distribution exhibiting maximum pore radius in the range of about 40–100 angstrom units.

7. The process of claim 1 wherein said support has a pore size distribution exhibiting peaks in the range of radii of about 10–250 angstrom units.

8. The process of claim 1 wherein said platinum metal is rhodium.

9. The process of claim 1 wherein said 6-hydroxy hydronaphthacene is 6-demethyltetracycline.

10. The process of preparing compounds of the formula:

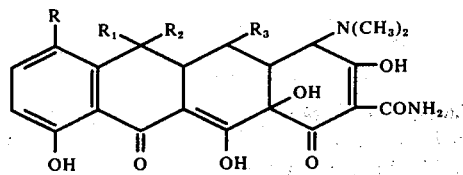

wherein R is selected from the group consisting of mono(lower alkyl)amino and di(lower alkyl)amino, $R_1$ is selected from the group consisting of hydrogen, α-methyl and β-methyl, $R_2$ is selected from the group consisting of hydrogen and β-hydroxy with the proviso that when $R_1$ is β-methyl then $R_2$ is hydrogen, $R_1$ and $R_2$ taken together is methylene; which comprises contacting a compound of the formula:

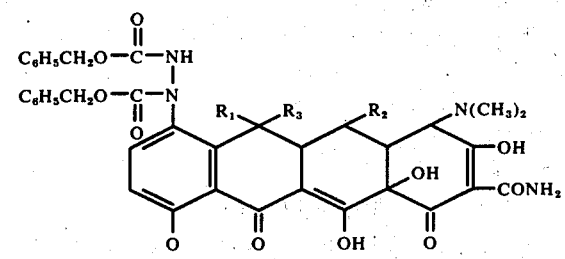

wherein $R_1$, $R_2$ and $R_3$ are as hereinabove defined, with a carbonyl compound of the formula:

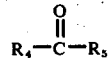

wherein $R_4$ and $R_5$ are the same or different and are each selected from the group consisting of hydrogen and lower alkyl, in the presence of hydrogen and a catalyst composition comprising a porous carbon particulate support comprising carbon black spheres in packed relationship and bonded with a carbonized binder, said spheres having a particle size in the range of about 80 to 5000 angstrom units and said particulate having a pore volume of at least about 0.2 cubic centimeter per gram and a pore size distribution exhibiting peaks at a pore radius in excess of 10 angstrom units and, carried on said support, an effective amount of a platinum group metal.

11. The process of preparing compounds of the formula:

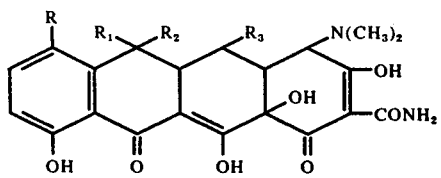

wherein R is selected from the group consisting of mono(lower alkyl)amino and di(lower alkyl)amino, $R_1$ is selected from the group consisting of hydrogen, α-methyl and β-methyl, $R_2$ is selected from the group consisting of hydrogen and β-hydroxy with the proviso that when $R_1$ is β-methyl then $R_2$ is hydrogen, $R_1$ and $R_2$ taken together is methylene, and $R_3$ is selected from the group consisting of hydrogen and hydroxy with the proviso that when $R_3$ is hydroxy then $R_1$ is methyl or $R_1$ and $R_2$ taken together is methylene; which comprises contacting a compound of the formula:

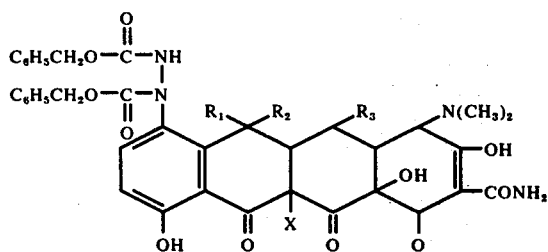

wherein $R_1$, $R_2$ and $R_3$ are as hereinabove defined and X is selected from the group consisting of fluoro, chloro and bromo, with a carbonyl compound of the formula:

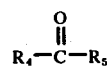

wherein $R_4$ and $R_5$ are the same or different and are each selected from the group consisting of hydrogen and lower alkyl, in the presence of hydrogen and a catalyst composition comprising a porous carbon particulate support comprising carbon black spheres in packed relationship and bonded with a carbonized binder, said spheres having a particle size in the range of about 80 to 5000 angstrom units and said particulate having a pore volume of at least about 0.2 cubic centimeter per gram and a pore size distribution exhibiting peaks at a pore radius in excess of 10 angstrom units, and carried on said support, an effective amount of a platinum group metal.

12. A process for the catalytic reduction of 2,4-dinitrotoluene to 2,4-diaminotoluene which comprises reducing a polar solvent solution of 2,4-dinitrotoluene with hydrogen in the presence of a catalyst composition comprising a porous carbon black spheres in packed relationship and bonded with a carbonized binder, said spheres having a particle size in the range of about 80 to 5000 angstrom units and said particulate having a pore size distribution exhibiting peaks at a pore radius in excess of 10 angstrom units and, carried on said support, an effective amount of a platinum group metal, until the corresponding 2,4-diaminotoluene is formed and recovering the 2,4-diaminotoluene so formed.

13. The process of claim 12 wherein said platinum metal is palladium.

* * * * *